US00PP15229P2

(12) United States Plant Patent
Cain et al.

(10) Patent No.: US PP15,229 P2
(45) Date of Patent: Oct. 12, 2004

(54) GRAPEVINE PLANT NAMED 'SUGRATWENTYEIGHT'

(50) Latin Name: *Vitis vinifera*
Varietal Denomination: Sugratwentyeight

(75) Inventors: David W. Cain, Bakersfield, CA (US); Michael J. Striem, Bakersfield, CA (US)

(73) Assignee: Sun World International, Inc., Bakersfield, CA (US)

( * ) Notice: Subject to any disclaimer, the term of this patent is extended or adjusted under 35 U.S.C. 154(b) by 15 days.

(21) Appl. No.: 10/619,013

(22) Filed: Jul. 10, 2003

(51) Int. Cl.[7] ..... A01H 5/00

(52) U.S. Cl. ..... Plt./205
(58) Field of Search ..... Plt./205

(56) References Cited

U.S. PATENT DOCUMENTS

PP11,749 P2 1/2001 Cain ..... Plt./205

*Primary Examiner*—Anne Marie Grunberg
*Assistant Examiner*—June Hwu
(74) *Attorney, Agent, or Firm*—Knobbe Martens Olson & Bear, LLP

(57) ABSTRACT

A new and distinct and mid-season ripening gravevine variety characterized by possessing naturally large, round, seedless grapes with a black tough and tannin skin. The grapes have a good eating quality, medium sugar content, and medium acidity.

1 Drawing Sheet

Latin name of the genus and species claimed: *Vitis vinifera.*
Variety denominations: 'Sugratwentyeight'.

BACKGROUND AND SUMMARY OF THE INVENTION

This invention relates to the discovery and asexual propagation of a new variety of grapevine as herein described and illustrated. The new variety was first hybridized by David W. Cain and Michael J. Striem in Kern County, Calif. The new variety 'Sugratwentyeight' is characterized by possessing naturally large, round, seedless grapes. The grapes have a black tough and tannin skin, with medium sugar content, and medium acidity, resulting in a good eating quality. The grapes ripen mid-season, approximately a week before 'Redglobe' (unpatented) and about 3–4 weeks after 'Thompson seedless' (unpatented) grape, when grown in the San Joaquin Valley, Calif.

The new variety was created by hybridization of two "seedless" grapes possessing small, abortive, vestigial ovules. From the initial population of hybrid ovules, embryo rescue procedures were used to produce a population from which the present variety was selected. The seed parent is 'Sun World Seedling 89145-062-244' (unpatented) variety and the pollen parent is 'Sun World Seedling 89014-019-280' (unpatented). The parent varieties were first crossed in May 1992, with the date of sowing being August 1992, and the date of first flowering being May 1994. The new 'Sugratwentyeight' variety was first asexually propagated by David W. Cain in January, 1995, in Wasco, Kern County, Calif., using hardwood cuttings.

The new variety 'Sugratwentyeight' is distinguishable from its seed parent 'Sun World Seedling 89145-062-244' by having a much smaller and softer seed trace. Additionally, the berry skin color of 'Sugratwentyeight' is much darker than the berry skin color of its seed-parent. The pollen parent 'Sun World Seedling 88014-019-280' tends to develop many shot berries, and the large berries are much softer than those of 'Sugratwentyeight'.

The new variety 'Sugratwentyeight' most nearly resembles the 'Sugrasixteen' variety U.S. Plant Pat. No. 11,749) in its berry skin color and ripening time. It can be distinguished from 'Sugrasixteen' by possessing round grapes with firm and juicy flesh, along with a tough skin having a tannin flavor. Additionally, the vine of the new variety 'Sugratwentyeight' is less vigorous and less productive than the vine of 'Sugrasixteen'. It also differs from 'Sugrasixteen' by having naturally larger and round berries, with much heavier bloom on the berry skin.

The new grapevine variety 'Sugratwentyeight' also resembles the 'Redglobe' grapevine variety by possessing large, rounded grapes. It can be distinguished from the 'Redglobe' variety by being seedless and by ripening about one week earlier than 'Redglobe'. The new grapevine variety can be further distinguished from 'Redglobe' by having a black berry color, and tough, tannic skin.

The new 'Sugratwentyeight' variety has been shown to maintain its distinguishing characteristics through successive asexual propagations by, for example, cuttings.

BRIEF DESCRIPTION OF THE FIGURE

The accompanying drawing in FIG. 1 illustrates in full color a typical cluster of berries, a young shoot, and a mature leaf blade of the new grapevine. The colors are as nearly true as is reasonably possible in a color representation of this type.

DETAILED BOTANICAL DESCRIPTION OF THE INVENTION

Figure 1:
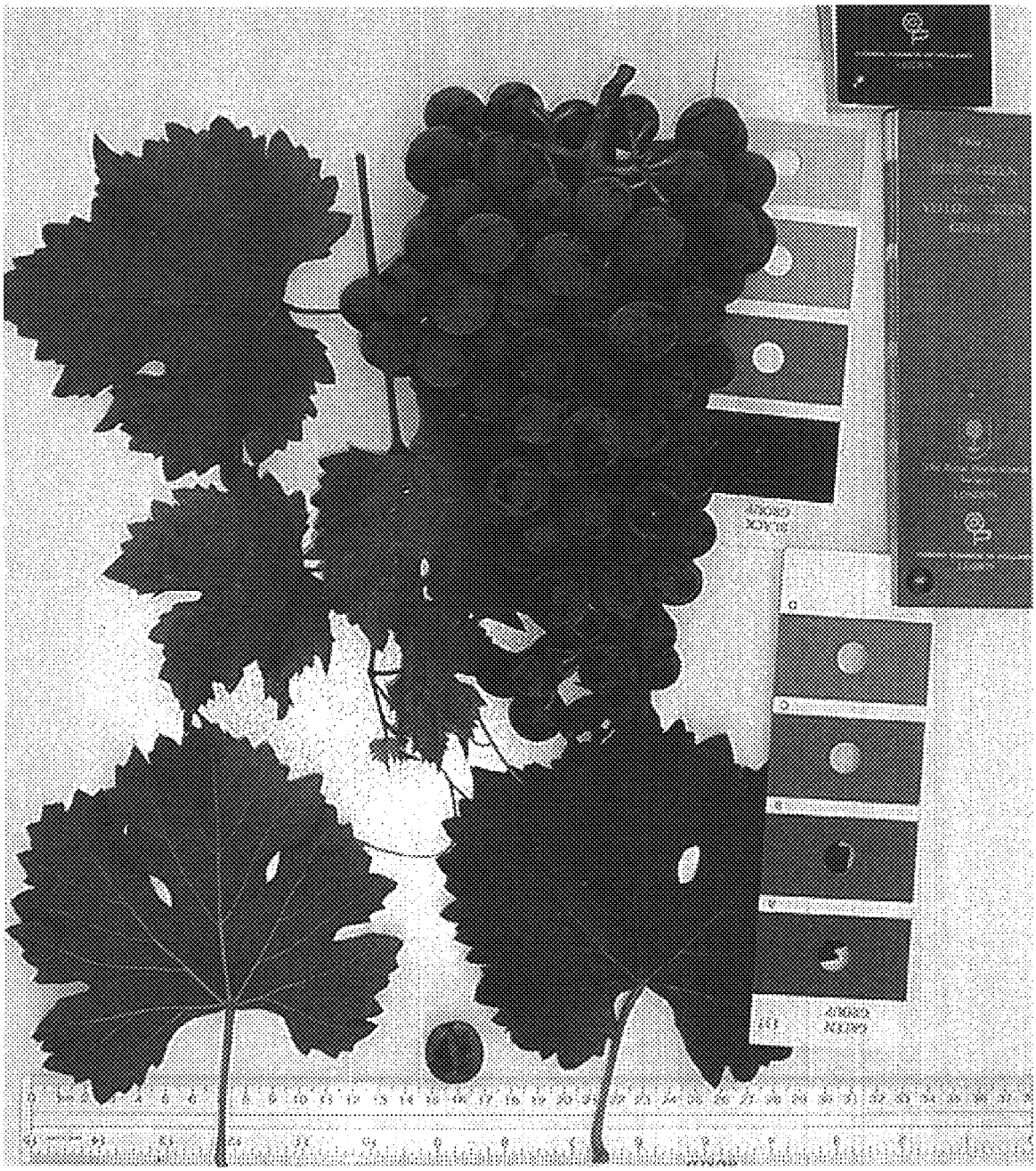

Throughout this specification, color names beginning with a smaller letter signify that the name of that color, as used in common speech, is aptly descriptive. Color names beginning with a capital letter designate values based upon The R.H.S. Colour Chart, published by The Royal Horticultural Society, London, England.

Many of the description values in this specification are based on and conform to those set forth by the International Board for Plant Genetic Resources Institute Grape Descriptors (*Vitis* spp.) of 1983 and/or 1997 which was developed in collaboration with the Office International de la Vigne et du Vin (OIV) and the International Union for the Protection of New Varieties of Plants (UPOV).

The descriptive matter which follows pertains to 9 year old 'Sugratwentyeight' plants grown in the vicinity of Wasco, Kern County, Calif., during 2002, and is believed to apply to plants of the variety grown under similar conditions of soil and climate elsewhere.

VINE

General:

*Height.*—Approximately 188 cm.
*Spread.*—Approximately 317 cm.
*Vigor.*—Medium.
*Density of foliage.*—Medium.
*Productivity.*—Productive.
*Root stock.*—Own Roots.

Trunk:

*Shape.*—Medium.
*Straps.*—Long.
*Surface texture.*—Shaggy.
*Inner bark color.*—About Greyed-orange 177B.
*Diameter* (*at approximately* 20 *cm above soil line*).—Approximately 68 mm.

SHOOTS

Young shoot:

*Form of tip.*—Fully open.
*Distribution of anthocyanin coloration of tip.*—Absent.
*Intensity of anthocyanin coloration of tip.*—Absent.
*Density of prostrate hairs on tip.*—Sparse.
*Density of erect hairs on tip.*—Absent.

Woody shoot:

*Shape.*—Medium.
*Internode length.*—Short — Approximately 30.92 mm.
*Width at node.*—Approximately 12.44 mm.
*Cross section.*—Circular.
*Surface.*—Smooth.
*Main color.*—About Greyed-orange 176C.
*Lenticels.*—Absent.
*Density of erect hairs on nodes.*—None or vary sparse.
*Density of erect hairs on internodes.*—None or very sparse.
*Growth of axillary shoots.*—Very weak — approximately 4.6 cm.

Flowering shoot:

*Vigor during flowering.*—Weak.
*Attitude during flowering on shoots which are not tied.*—Semi-drooping.
*Color of dorsal side of internodes.*—About Yellow-green 144A with stripes of about Greyed-purple 183B.
*Color of ventral side of internodes.*—About Yellow-green 144A with stripes of about Greyed-purple 183B.
*Color of dorsal side of nodes.*—About Yellow-green 144A with stripes of about Greyed-purple 183B.
*Color of ventral side of nodes.*—About Yellow-green 144A with stripes of about Greyed-purple 183B.
*Density of erect hairs on nodes.*—None.
*Erect hairs on internode.*—Absent.
*Density of prostrate hairs on nodes.*—None.
*Density of prostrate hairs on internodes.*—Absent.
*Anthocyanin coloration of buds.*—Absent.

Tendrils:

*Distribution on the shoot at full flowering.*—Discontinuous.
*Thickness.*—Thin.
*Color.*—About Yellow-green 144B.
*Form.*—Bifurcated.
*Number of consecutive tendrils.*—Up to two.
*Length of tendril.*—Medium — approximately 22 cm.

LEAVES

Young leaves:

*Color of upper surface of first 4 distal unfolded leaves.*—Yellow with bronze spots.
*Average intensity of anthocyanin coloration of six distal leaves prior to flowering.*—Medium to strong.
*Density of prostrate hairs between veins at lower surface of 4th distal unfolded leaf.*—Absent.
*Density of erect hairs between veins at lower surface of 4th distal unfolded leaf.*—Absent.
*Density of prostrate hairs on veins at lower surface of 4th distal unfolded leaf.*—Very sparse.
*Density of erect hairs on veins at lower surface of the 4th distal unfolded leaf.*—Absent.

Mature leaves:

*Average length.*—Approximately 150 mm.
*Average width.*—Approximately 155 mm.
*Size of blade.*—Large.
*Shape of blade.*—Pentagonal.
*Number of lobes.*—5.
*Anthocyanin coloration of main veins on the upper side of the blade.*—Weak.
*Mature leaf profile.*—Undulate.
*Blistering surface of blade upper surface.*—Medium.
*Leaf blade tip.*—In the plane of the leaf.
*Undulation of margin.*—Medium.
*Apex.*—Cuspidate.
*Thickness.*—Medium.
*Undulation of blade between main and lateral veins.*—Only near petiole.
*Shape of teeth.*—Mixture of both sides straight and both sides convex.
*Length of teeth.*—Long.
*Ratio length/width of teeth.*—Large.
*General shape of petiole sinus.*—Half open.
*Tooth at petiole sinus.*—Absent.
*Petiole sinus limited by veins.*—Absent.
*Shape of upper lateral sinus.*—Lobes slightly overlapping.
*Depth of upper lateral sinus.*—Medium.
*Density of prostrate hairs between veins on lower surface of blade.*—Absent.
*Density of erect hairs between veins on lower surface of blade.*—Absent.
*Density of prostrate hairs on main veins on lower surface of blade.*—Sparse.
*Density of erect hairs on main veins on lower surface of blade.*—None or very sparse.
*Density of prostate hairs on main veins on upper surface of blade.*—Absent.
*Autumn coloration of leaves.*—About Greyed-orange 163B. (Note: Autumn leaf coloration is slow to develop. Normally frost kills leaves before extensive color change.)

Upper surface:

*Color.*—About Green 137C.
*Surface texture.*—Rugose.
*Surface appearance.*—Dull.
*Goffering of blade.*—Present.

Lower surface:

*Color.*—About Green 137D.
*Anthocyanin coloration of main veins on lower leaf surface.*—Weak.
*Glossiness.*—Weak.
*Pubescence.*—Few.
*Surface texture.*—Smooth.
*Surface appearance.*—Semi-glossy.

Petiole:

*Length of petiole.*—Medium — approximately 9.35 cm.
*Length of petiole compared to middle vein.*—Slightly shorter.
*Density of prostrate hairs on petiole.*—None.
*Density of erect hairs on petiole.*—None.
*Shape of base of petiole sinus.*—V-shaped.

Buds:

*Shape.*—Pointed.
*Size.*—Medium. — Approximately 4 mm by approximately 6 mm.
*Position.*—Slightly held out — (at approximately at 45° angle).
*Cane bud fruitfulness.*—Basal most fruitful.
*Time of bud burst.*—Medium.

FLOWERS

General:

*Flower sex.*—Hermaphrodite.
*Length of first inflorescence.*—Long.
*Position of first flowering node.*—$3^{rd}$.
*Number of inflorescences per shoot.*—Up to 1.
*Date of full bloom.*—May 9, 2002.
*Time of bloom.*—Early.
*Size* (*diameter of fully open flower*).—Medium.

FRUIT

General:

*Ripening period.*—Medium — ripens about 3–4 weeks after 'Thompson seedless' grape, when grown in the San Joaquin Valley, Calif.
*Use.*—Fresh market.
*Keeping quality.*—Good.
*Disease resistance.*—Neither resistance nor susceptibility to diseases and pests has been observed in this cultivar.
*Shipping quality.*—Medium.
*Date of first harvest.*—Aug. 22, 2002.
*Solids-Sugar.*—Medium (approximately 18%).
*Refractometer test.*—Approximately 19.0.
*Acid.*—Medium — approximately 4.24 grams/L tartaric acid.
*Juice pH.*—Approximately 4.32.

Cluster:

*Bunch size* (*peduncle excluded*).—Large.
*Bunch length* (*peduncle excluded*).—Long — approximately 29 cm.
*Bunch width.*—Approximately 16.3 cm.
*Bunch weight.*—High — approximately 653 g.
*Bunch density.*—Loose.
*Number of berries.*—Approximately 112.5.
*Form.*—Conical.

Peduncle:

*Length of peduncle.*—Very short — approximately 29.8 mm.
*Lignification of peduncle.*—Weak.
*Color.*—About Greyed-purple 183B.

Berry:

*Size.*—Large.
*Uniformity of size.*—Variable.
*Berry weight.*—Very high — approximately 6.12 g.
*Shape.*—Round.
*Presence of seeds.*—Rudimentary — approximately 1.12 mg.
*Cross section.*—Circular.
*Length.*—Approximately 24.0 mm.
*Width.*—Approximately 20.8 mm.
*Skin color* (*without bloom*).—About Black 202A.
*Coloration of flesh.*—Transparent greenish.
*Juiciness of flesh.*—Very juicy.
*Berry firmness.*—Firm.
*Particular flavor.*—None.
*Bloom* (*cuticular wax*).—Strong.
*Pedicel length.*—Intermediate — approximately 0.94 cm.
*Berry separation from pedicel.*—Easy.
*Visibility of hilum.*—Slightly visible.

Skin:

*Thickness.*—Thick.
*Thick.*—Tough.
*Reticulation.*—Absent.
*Roughness.*—Absent.
*Tenacity.*—Tenacious to flesh.

What is claimed is:

1. A new and distinct variety of grapevine plant named 'Sugratwentyeight' as herein illustrated and described.

* * * * *